(12) United States Patent
Kogure et al.

(10) Patent No.: US 6,807,844 B2
(45) Date of Patent: Oct. 26, 2004

(54) DUST SAMPLING DEVICE

(75) Inventors: Nobuyuki Kogure, Tsukuba (JP);
Masaaki Shirahase, Tsukuba (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 42 days.

(21) Appl. No.: 10/094,304

(22) Filed: Mar. 11, 2002

(65) Prior Publication Data

US 2002/0166365 A1 Nov. 14, 2002

(30) Foreign Application Priority Data

May 11, 2001 (JP) .................................. 2001-142137

(51) Int. Cl.[7] .............................................. G01N 37/00
(52) U.S. Cl. .................................. 73/28.01; 73/31.07
(58) Field of Search ............................. 73/28.01, 28.05, 73/31.03, 31.07, 863.22, 863.23, 863.71

(56) References Cited

U.S. PATENT DOCUMENTS

| | | |
|---|---|---|
| 4,091,835 A | 5/1978 | Frampton |
| 4,167,117 A | 9/1979 | Stokley et al. |
| 5,856,623 A | 1/1999 | Ahn et al. |

FOREIGN PATENT DOCUMENTS

| | | |
|---|---|---|
| DE | 4237009 A1 | 5/1994 |
| JP | 56-2191 Y2 | 1/1981 |

OTHER PUBLICATIONS

Enviornmental protection measuring instruments in modular technology, Ninth Edition; (2000).

Primary Examiner—Hezron Williams
Assistant Examiner—Katina Wilson
(74) Attorney, Agent, or Firm—Birch, Stewart, Kolasch & Birch, LLP

(57) ABSTRACT

A dust sampling device having a sampling nozzle is provided. The nozzle is provided with an inlets the diameter of which is variable. The diameter of the nozzle can be instantaneously changed, while keeping constant a sampling flow rate within a measuring device as the nozzle is introduced into a chimney or a duct in response to a change in flue gas flow velocity, to thereby maintain an uniform sampling rate in the nozzle. The nozzle is connected to a dust measuring device and is inserted into an interior of an flue gas passage. The diameter of the nozzle can be changed so as to keeping sampling gas flow rate determined by the dust measuring device constant at the sampling velocity corresponding to the flow velocity of the flue gas. The flue gas sampled through the nozzle is introduced into the dust measuring device.

8 Claims, 3 Drawing Sheets

51. VARIOUS MEASURING DEVICES  52. COOLER  53. DEHUMITIDATOR
54. SILICAGEL  55. RECIRCULATION PUMP  56. BUFFER
57. MASS FLOW METOR  58. SAMPLING PUMP  59. GAS METER
60. AIR CLEANING SYSTEM

DUST SAMPLING DEVICE

BACKGROUND OF THE INVENTION

1. Field of the Invention

The present invention relates to a dust sampling device, more particularly, to a dust sampling device having a sampling nozzle with a variable nozzle-inlet diameter, wherein a dust sample indispensable for measuring physical characteristics, such as, for example, a concentration, a particle size and a chemical component of particulate substances (hereinafter referred to as "dust") contained in a flue gas discharged from a factory, an automotive vehicle and the like is sampled into the dust sampling device under a predetermined sampling flow rate at the same velocity as a flow velocity of the flue gas. The sampling at the same velocity as the flow velocity of the flue gas is referred to as "isokinetic sampling" hereinafter.

2. Description of the Related Art

Recently, much attention has been devoted to the particle size of the dust contained in the flue gas to determine physical properties of the flue gas With the increased demand of the dust measurement in various sources, a problem associated with a conventional measuring method it, for example, a multi-cyclone utilizing a centrifugal force or a measuring method such as Cascade Impactor or Andersen stack sampler utilizing inertia force of particles has been pointed out. The problem of the conventional measuring methods is that the sampling flow rate within the measuring device should be kept constant throughout the operation in case where the dust is sorted according to the particle diameter. Namely, when the dust sample is to be collected from the flue gas at the isokinetic sampling flow rate, it is necessary to measure the flow velocity, the temperature, the pressure, the moisture content and the like of the flue gas in advance, to obtain the isokinetic sampling flow rate in accordance with the following formula based upon a diameter of the sampling nozzle inlet to be used and to perform the sampling and sorting operation of the dust sample for a predetermined period of time.

$$qm = \frac{\pi}{4} d^2 v \left(1 - \frac{X_w}{100}\right) \frac{273 + \theta m}{273 + \theta s} \times \frac{Pa + Ps}{Pa + Pm} \times 0.06$$

where gm is the isokinetic sampling flow rate (l/min)

d is the diameter of the nozzle inlet (mm)

v is the flow velocity of the flue gas (m/s)

Xw is the moisture content (%)

θm is the temperature of the sampled gas at a dry gas meter (° C.)

θs is the temperature of the flue gas (° C.)

Pa is the atmospheric pressure (mmHg)

Ps is the static pressure of the flue gas (mmHg)

Pm is the gauge pressure in a dry gas meter of the sampled gas (mmHg)

Accordingly, in case where the flue gas varies, it is necessary to re-calculate the isokinetic sampling flow rate, which creates problems in measurement operation and requires a great amount of labor and time resulting from the interruption of the measurement, and the exchange of the sampling nozzle.

In the dust measurement in the flue gas (concentration, particle size distribution, chemical composition and the like), it is indispensable for the sampling work to perform the sampling of the flue gas sample through the sampling nozzle at the same flow velocity as that of the flue gas contrary to the gas measurement in the flue gas. If the isokinetic sampling is deviated from a predetermined allowable range (−5% to +10% of the flue gas flow velocity) due to the inertia effect resulting from the particle size, flow rate and density of the dust, there is caused a large error in entrainment of the dust particles into the sampling nozzle. For this reason, the flow velocity, temperature, pressure, and moisture content of the flue gas are measured in advance so that the diameter of the sampling nozzle inlet to be used is selected, to thereby calculate the isokinetic sampling flow rate. Thereafter, the sampling of the dust is performed (this method is generally referred to as "normal sampling method").

In contrast, FIG. 3 shows an equilibrium sampling method (see Japanese Utility Model Examined Publication No. Sho 56-2191). In this method, a dynamic pressure corresponding to a flow velocity of the flue gas at the sampling point within a duct 21 is displayed at a slant water head meter 38 through pressure feed pipes 37 and 40. A pump 27 is operated to sample (suck) the flue gas within the duct 21 from a sampling nozzle 24. In this manner, an average pressure difference in gas between the upstream and downstream sides of the throttle of a venturi pipe 25 is displayed at a slant water head meter 33. A bypass cock 29 is adjusted so that the average pressure difference indicated in the slant water head meter 33 is identified with the dynamic pressure indicated in the slant water head meter 38, whereby the flue gas is sampled from the sampling nozzle 24 at the same flow velocity as the flow velocity of the flue gas within the duct 21 and the dust is collected into a dust collector 23. An amount of sample flue gas is accumulated and calculated by a gas meter 29. A mass concentration of the dust contained in the flue gas is obtained immediately from the amount of the flue gas sampled and the mass of the dust. This equilibrium type sampling method is useful, because the isokinetic sampling is immediately performed only by identifying the dynamic pressure or the static pressure of the sample gas within the nozzle with the dynamic pressure or the static pressure of the flue gas.

In the conventional measuring method described above, the sampling nozzle is fixed and the isokinetic sampling is performed by changing the sampling flow rate.

In the measuring device in which the sampling flow rate within the measuring device must be kept constant, the sampling flow rate within the measuring device is changed, if the flue gas flow velocity is changed which results in changes in the gas flow rate to be sampled at a velocity corresponding to the flow velocity of the flue gas. This creates a problem in measurement.

In order to overcome such a problem, a flue gas circulation system as shown in FIG. 4 is currently proposed. In this system, in order to keep the sampling flow rate within the measuring device constant, a part of the sample gas is circulated and introduced forward in the measuring device and merged and circulated Smith the gas sampled at an uniform velocity from the nozzle inlet. However, this system is not practical in operation, because it is required to perform cleaning of the circulated flue gas, complicated and enlarged the circulation system, additional equipment such as circulation pumps, and so on. Accordingly, this system is not suitable for the practical use in the on-the-spot measurement in a factory.

According to the present invention, there is provided a measuring device in which the sampling flow rate within the device is kept constant in principle during the dust measurement in the flue gas, for example, a filter oscillation monitor, a carbon particle monitor and the like for use in a concentration measurement field, a cascade impactor, a multi-cyclone and the like for use in a particle size distribution measurement field, and a JIS type dust sampler and the like for use in a dust sampling field for chemical analyses, wherein a remarkable error arises due to non-uniform sampling in case where the flue gas varies, and the measurement is invalidated or to be conducted again.

SUMMARY OF THE INVENTION

Accordingly, an object of the present invention is to provide a dust sampling device which is capable of instantaneously changing an opening diameter of a nozzle in response to the change in the flow velocity of the flue gas and to maintain an sokinetic sampling while keeping the sampling flow rate in a measuring device constant as the sampling nozzle is inserted into a chimney or a duct. Namely, in case where the flow rate v of the flue gas is changed, the diameter d of the nozzle inlet is changed so that the relationship, $d^2 v =$ constant, is kept.

The dust sampling device according to the present invention includes the sampling nozzle with a variable nozzle-inlet diameter. The nozzle is connected to a dust measuring device and a sampling device, and is inserted into an interior of a flue gas passage. The opening diameter of the nozzle is variable so as to keep the sampling flow rate determined by the dust sample measuring device constant, and to have the same sampling velocity as the flow velocity of the flue gas. The flue gas sampled through the nozzle is introduced into the dust measuring device.

BRIEF DESCRIPTION OF THE DRAWINGS

The foregoing features of the present invention may be more fully understood from the following detailed description, read in conjunction with the accompanying drawings, wherein.

DESCRIPTION OF THE PREFERRED EMBODIMENTS

An embodiment of the present invention will now be described with reference to FIGS. 1 and 2.

Figure 1:
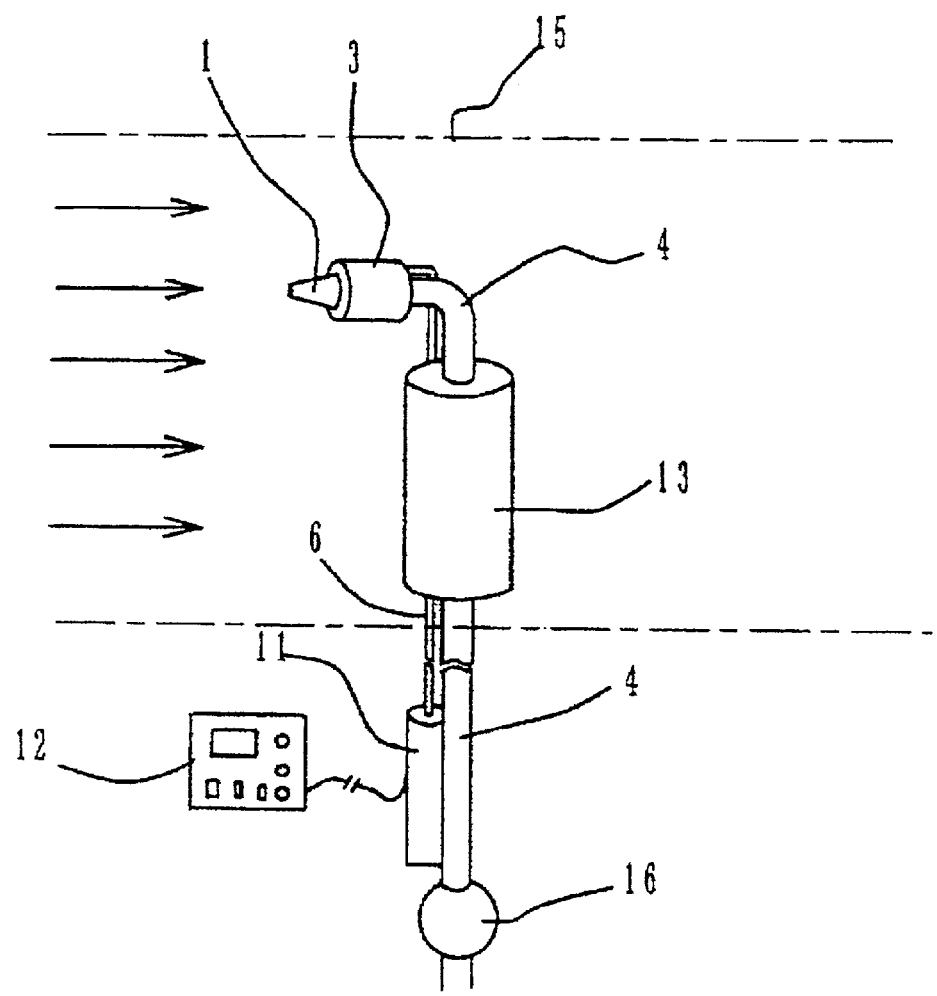
FIG. 1 is a frontal view showing an overall structure of a dust sampling device having a sampling nozzle with a variable nozzle-inlet diameter in accordance with an embodiment of the present invention.

FIG. 1 shows an overall structure of the dust sampling device according to an embodiment of the present invention. A nozzle (sampling nozzle) 1, the diameter of which is variable, is disposed within a flue gas duct 15 in which the dust particle distribution is to be measured. A particle size distribution measuring device 13 such as cascade impactor or a multi-cyclone is arranged at a point midway of a joint sleeve 4. A sampling pump 16 is provided on the joint sleeve 4 downstream of the particle size distribution measuring device 13. The rotary shaft 6 is connected to a drive device 11 arranged behind the joint sleeve 4, and rotated in accordance with instructions of a controlling unit 12.

Figure 2:
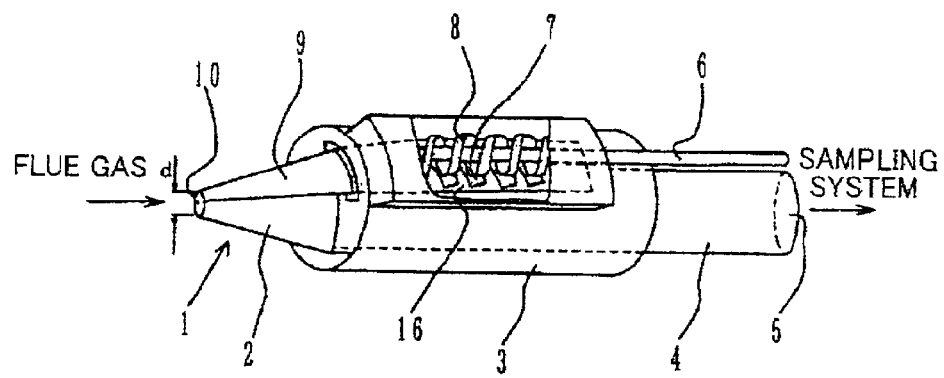
FIG. 2 is a front view showing the nozzle shown in FIG. 1 in detail.
Figure 3:
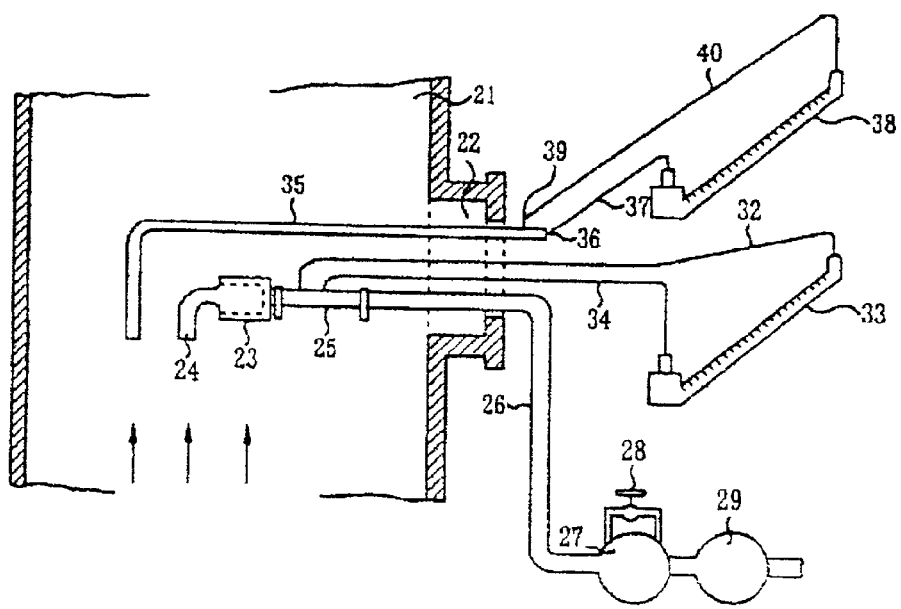
FIG. 3 is a schematic view showing a conventional equilibrium sampling method.
Figure 4:
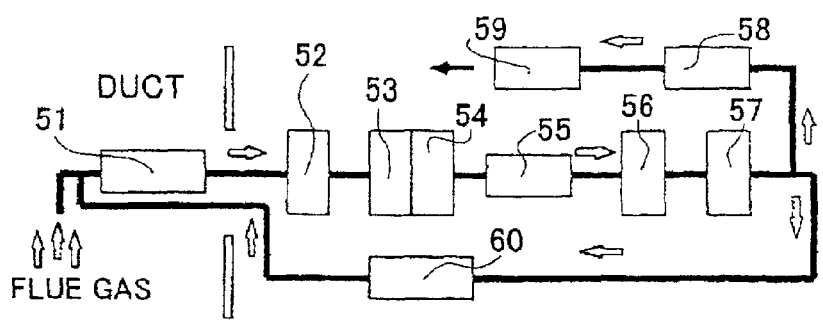
FIG. 4 is a schematic view showing a conventional flue gas recirculation system.

FIG. 2 shows the nozzle 1 in detail. The nozzle 1 having the inlet 10, the diameter of which is variable, is composed of a lower stationary nozzle and an upper slippage nozzle 9. The slippage nozzle 9 has an extension 16 whose rear part extends rearwardly. The extension 16 is provided with drive gear receiving teeth 7 engaging with a drive gear 8 of the slippage nozzle 9 formed at a rotary shaft 6 so that the slippage nozzle 9 may be moved back and forth. When the slippage nozzle 9 is moved back and forth, the terminating front end of the slippage nozzle 9 is moved back and forth with respect to the stationary nozzle 2. Thus, an opening diameter d of the nozzle 1 can be changed as the slippage nozzle 9 moves back and forth, while keeping the inlet 10 in a circular shape. The rotary shaft 6 is connected to a drive device 11 arranged behind the joint sleeve 4, and rotated in accordance with instructions of a controlling unit 12.

The rear portion of the nozzle 1 is connected to the joint sleeve 4 provided with a sample gas passage 5 communicating with the particle size distribution measuring device 13. Also, the drive gear 8 of the slippage nozzle 9 and the drive gear receiving teeth 7 are disposed within a protective tube 3. It is to be understood that means for changing the opening diameter d of the inlet 10 of the nozzle 1 is not limited to that described above, and any conventional driving devices can be used.

In order to measure the particle size distribution of the dust in the flue gas using the dust sampling device of the present invention, the flow velocity v of the flue gas is monitored by means of a flow velocity measuring device, such as, a Pitot tube (not shown). In addition, a temperature θs, a pressure Ps and a moisture content Xw of the flue gas are supervised if there is a possibility that these factors would be changed. The flue gas is sampled at the same velocity as the flow velocity of the flue gas from the nozzle 1 so as to keep the sampling flow rate determined by the particle size distribution measuring device 13, and introduced into the particle size distribution measuring device 13 through the sample gas passage 5. In case where the flow velocity of the flue gas is changed, the opening diameter d of the nozzle 1 is subjected to change so as to keep constant the sampling flow rate within the particle size distribution measuring device 13 to attain the isokinetic sampling while keeping the predetermined sampling flow rate.

According to the dust sampling device of the present invention, the nozzle having the inlet, the diameter of which is variable, is connected to any dust measuring devices, and the diameter of the nozzle is changed so as to obtain the isokinetic sampling flow rate in response to the variation of the flue gas while keeping constant the sampling flow rate within the device, whereby the isokinetic sampling of the flue gas in the measuring device can be instantaneously attained to make it possible to sample the dust sample inherent in the flue gas.

As will be readily appreciated, various modifications and combinations of the features described above can be employed without departing from the present invention. Accordingly, the foregoing description of the preferred embodiments should be taken as illustrating rather than as limiting the present invention as defined by the claims.

What is claimed is:

1. A dust sampling device comprising:
   a sampling nozzle having an inlet, said nozzle being inserted into an interior of a flue gas passage;
   a dust measuring device connected to said nozzle; a controlling unit;
   a sampling device for introducing the flue gas in said flue gas passage into said dust measuring device through said nozzle;

wherein said controlling unit adjusts a diameter of the inlet so the flue gas in said nozzle is at essentially the same flow velocity as the flow velocity of the flue gas in said flue gas passage, while maintaining a predetermined sampling flow rate determined by said dust measuring device.

2. A dust sampling device according to claim 1, wherein said nozzle is composed of a stationary nozzle and a slippage nozzle.

3. A dust sampling device according to claim 1, wherein said controlling unit adjusts the diameter of the inlet so the flue gas in said nozzle is isokinetic with the flue gas in the flue gas passage.

4. A dust sampling device comprising:

a sampling nozzle having an inlet, said nozzle being inserted into an interior of a flue gas passage;

a dust measuring device connected to said nozzle;

a sampling device for introducing the flue gas in said flue gas passage into said dust measuring device through said nozzle;

wherein said inlet is variable in diameter so as to introduce the flue gas into said nozzle at a velocity corresponding to the flow velocity of the flue gas in said flue gas passage, while maintaining a predetermined sampling flow rate determined by said dust measuring device, wherein said nozzle is composed of a stationary nozzle and a slippage nozzle, and wherein a gear mechanism including a rotary shaft provided with a gear and teeth for driving said slippage nozzle.

5. A dust sampling method comprising the steps of:

inserting a sampling nozzle having an inlet into an interior of a flue gas passage;

changing a diameter of said inlet with a controlling unit so as to introduce a flue gas into said nozzle, wherein the flue gas in said nozzle is at essentially the same velocity as the flow velocity of the flue gas, while keeping the sampling flow rate constant; and introducing the flue gas into a dust measuring device through said nozzle.

6. A dust sampling method according to claim 5, wherein the diameter of the nozzle inlet is changed by providing a nozzle with a stationary nozzle and a slippage nozzle and moving said slippage nozzle back and forth with respect to said stationary nozzle.

7. A dust sampling method according to claim 5, wherein the flue gas in said nozzle is isokinetic with the flow velocity of the flue gas in the flue gas passage.

8. A dust sampling method comprising the steps of:

inserting a sampling nozzle having an inlet into an interior of a flue gas passage;

changing a diameter of said inlet so as to introduce a flue gas into said nozzle at a velocity corresponding to the flow velocity of the flue gas, while keeping the sampling flow rate constant; and introducing the flue gas into a dust measuring device through said nozzle, wherein the diameter of the nozzle inlet is changed by providing a nozzle with a stationary nozzle and a slippage nozzle and moving said slippage nozzle back and forth with respect to said stationary nozzle, and wherein said slippage nozzle is moved by a gear mechanism including a rotary shaft provided with a gear and teeth.

* * * * *